United States Patent [19]

Yokoyama et al.

[11] Patent Number: 4,661,448

[45] Date of Patent: Apr. 28, 1987

[54] METHOD FOR PRODUCING REDUCED-FORM COENZYME

[75] Inventors: Sadaji Yokoyama; Shinichiro Suye, both of Ootsu, Japan

[73] Assignee: Takara Shuzo Co., Ltd., Kyoto, Japan

[21] Appl. No.: 711,213

[22] Filed: Mar. 13, 1985

[30] Foreign Application Priority Data

Mar. 28, 1984 [JP] Japan .................................. 59-60100
May 4, 1984 [JP] Japan .................................. 59-89982
Sep. 20, 1984 [JP] Japan ................................ 59-197081

[51] Int. Cl.$^4$ ...................... C12N 19/36; C12N 9/04; C12Q 1/32
[52] U.S. Cl. ........................................ 435/90; 435/190
[58] Field of Search ........................... 435/90, 189, 190

[56] References Cited

U.S. PATENT DOCUMENTS 4,550,079 10/1985 Röder et al. ........................ 435/189

FOREIGN PATENT DOCUMENTS 101491 8/1979 Japan ..................................... 435/90

Primary Examiner—Lionel M. Shapiro

[57] ABSTRACT

A method for producing a reduced-form coenzyme by reacting malic acid with either nicotinamide adenine dinucleotide or nicotinamide adenine dinucleotide phosphate in the presence of malate dehydrogenase to obtain the corresponding reduced product. The reaction is preferably carried out under reduced pressure, while removing carbon dioxide, formed during the reaction, from the reaction system.

5 Claims, No Drawings

METHOD FOR PRODUCING REDUCED-FORM COENZYME

The present invention relates to a method for producing reduced-form nicotinamide adenine dinucleotide (hereinafter referred to as NADH) and reduced-form nicotinamide adenine dinucleotide phosphate (hereinafter referred to as NADPH). More particularly, the present invention relates to a method for producing NADH and NADPH by enzymatically reducing nicotinamide adenine dinucleotide (hereinafter referred to as NAD) and nicotinamide adenine dinucleotide phosphate (hereinafter referred to as NADP), respectively.

NADH and NADPH are well known to be a substance which is important as a coenzyme of dehydrogenase, and also they are used for detection of various kinds of dehydrogenase reaction because of their characteristic ultraviolet absorption. That is, while NADH and NADPH, which are of a reduced form, show a remarkable absorption at 340 nm, NAD and NADP, which are of an oxidized form, show no such absorption, and therefore when NADH and NADPH are used as a coenzyme for dehydrogenase reaction in the enzymatic assay of various kinds of substance in living body such as pyruvic acid, oxaloacetic acid and ammonia in serum and urine, they can be made a distinct indicator for said substances.

NADH and NADPH are obtained by reducing NAD and NADP, respectively. For reduction of NAD and NADP, there is also a chemical method using a reducing agent such as sodium dithionite ($Na_2S_2O_4$). In this method, however, various isomers having an inhibitory action on the enzyme reaction are produced, so that sodium dithionite cannot be used as a biochemical reagent.

On the other hand, since enzymatic reduction with dehydrogenases of which the coenzyme is NAD or NADP, produces no such isomers, it is now generally used for the production of NADH and NADPH.

For enzymatic reduction of NAD, there is a method using formate dehydrogenase [Japanese Patent Application Kokai (Laid-open) No. 101491/1979]. But, it is a problem to use formic acid in commercial production because the acid is a volatile liquid having a strong irritating odor and corrosive property, and because it causes diseases when put on skin.

For enzymatic reduction of NADP, there are reported various methods as follows: A method using glucose-6-phosphate dehydrogenase (Izumi, et al., Collection of Lectures on the Meeting of the Agricultural Chemical Society of Japan in 1983, pp. 358); a method using glucose dehydrogenase (Izumi, et al., Collection of Lectures on the Meeting of the Agricultural Chemical Society of Japan in 1984, pp. 595); a method using methanogenic bacteria [Eguchi, et al., Agricultural and Biological Chemistry, Vol. 47, pp. 2941–2943 (1984)]; and the like.

In these methods, however, an alkali condition of pH=about 9 is made essential to effective progress of the reaction, and such condition has adverse effects on MAD(P) and NAD(P)H, being undesirable in terms of the yield of the desired product.

In view of the problems described above, the present inventors have endeavored to establish a manufacturing method meeting the following conditions, with the object of effecting the commercial production of NAD(P)H:

(1) A compound used as a substrate shall be cheap and not dangerous to handle.
(2) The reduction shall be carried out in a neutral pH region. This condition is inevitable considering that NAD and NADP are easily decomposed at the alkali side, and that NADH and NADPH are easily decomposed at the acid side. Consequently, what is essential to the reaction (i.e. reduction) is that the equilibrium trends toward the formation of NADH or NADPH within a pH range of 6 to 8.

Briefly speaking, the present invention provides a method for producing NADH and NADPH, and it is characterized in that NADH or NADPH is obtained by reacting NAD or NADP with malic acid in the presence of malate dehydrogenase.

The reaction of malate dehydrogenase is expressed by the following equation:

L-Malic acid + NAD(P) 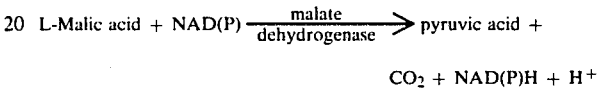 pyruvic acid + $CO_2$ + NAD(P)H + $H^+$

This reaction will thoroughly proceed in an almost neutral region of pH=about 7.5, so that small amounts of substrate and enzyme will suffice, and also decomposition of NAD(P) and NAD(P)H in the course of reaction is inhibited. Further, when this reaction is carried out under reduced pressure thereby to remove carbon dioxide gas formed by reaction from the reaction system, the reaction becomes easier to proceed toward the formation of NAD(P)H, and as a result, production of NAD(P)H can be carried out very smoothly.

In the present invention, enzymes of any source may be used, if they are malate dehydrogenase belonging to Enzyme No. EC 1.1.1.38, EC 1.1.1.39 or EC 1.1.1.40. An enzyme belonging to EC 1.1.1.38 can be obtained, for example, from *Escherichia coli* or *Lactobacillus arabinosus* by the well-known method (refer to Enzyme Handbook, pp. 14, published from Asakura-shoten Co. in 1982). An enzyme belonging to EC 1.1.1.39 is obtained, for example, from *Pseudomonas diminuta* (refer to Japanese Patent Application No. 197080/1984). An enzyme of EC. 1.1.1.40 is obtained, for example, from pigeon liver (refer to Methods in Enzymology, Vol. 1, 739–753, 1955).

As the source of enzyme, cell itself having a malate dehydrogenase activity previously improved in membrane permeability by freezing and thawing, treatment with organic solvent or surface active agent, or other treatments may be used as such.

For the immobilization of malate dehydrogenase, the well-known immobilizing methods such as the polyacrylamide method, the method using glutaraldehyde and a reacting agent or polysaccharides such as carrageenan, and the like may be used.

The enzyme activity can be measured from an increase in the absorbance at 340 nm of NAD(P)H produced by the reaction. Components contained in 1 ml of the reaction solution are 20 μmole of L-malic acid, 10 μmole of magnesium chloride, 0.35 μmole of NAD or 0.20 μmole of NADP and 50 μmoles of HEPES (N-2-hydroxyethylpiperazine-N'-2-ethanesulfonic acid)-/KOH buffer (pH, 7.4). The enzyme solution is added to this reaction solution to carry out reaction for 30 minutes. One unit, U, of enzyme activity is defined as enzyme activity to decompose 1 μmole of a substrate per minute.

The reaction of the present invention is carried out, preferably, at a pH of 6 to 8 in water or a buffer solution (e.g. HEPES, Tris-HCl buffer, phosphate buffer). It is preferred to add a $Mg^{++}$ ion (e.g. $MgCl_2$, $MgSO_4$) to the reaction solution. The amount of NAD or NADP added to the reaction solution is preferably 0.05 to 10% (w/v) and that of malic acid added thereto is preferably 0.02 to 5% (w/v). Malate dehydrogenase is added after adding NAD or NADP and malic acid. Malic acid may be any of L-malic acid and DL-malic acid. The reaction is generally carried out at 20° to 40° C. for several hours to several ten hours.

Preparation of malate dehydrogenase is carried out as follows using, for example, *Pseudomonas diminuta* IFO-13182. A nutrient medium comprising 1 g/dl of D-malic acid, 0.03 g/dl of $MgSO_4.7H_2O$, 0.3 g/dl of citric acid, 1.5 g/dl of $K_2HPO_4$, 0.53 g/dl of $Na(NH_4)HPO_4$, 0.6 g/dl of NaOH, 0.1 g/dl of yeast extract and 1 g/dl of peptone is added to ten 2-liter Erlenmeyer flasks at a rate of 500 ml per flask and sterilized at 120° C. for 15 minutes. Each medium is inoculated with the strain above, followed by shaking culture at 30° C. for 24 hours. After the culture is finished, the culture broth is centrifuged to collect the cell. The cell is washed, suspended in 1000 ml of a 40 mM phosphate buffer solution (pH, 7.4) containing 10 mM of 2-mercaptoethanol (hereinafter referred to as 2-ME) and 2 mM of ethylenediamine tetraacetic acid disodium salt (hereinafter referred to as EDTA-2Na) and disintegrated at 5° C. or less for 10 minutes by means of a 9 KHz ultrasonic disintegrator (produced by Kubota Seisakusho Co.). The solution after disintegration is centrifuged, and the resulting supernatant solution is used as an enzyme solution in the subsequent experiment.

The solution subjected to ultrasonic disintegration is contaminated with NADH oxidase which re-oxidizes NADH produced from NAD, so that it is necessary to inactivate the oxidase by heat treatment at 50° C. for 1 hour. Malate dehydrogenase activity is not affected at all under this condition.

Malate dehydrogenase may be used in the form of extract as described above, but the cell may also be used after making it highly permeable. The permeability of the cell improves by freezing and storing the cell overnight in the coexistence of a nonionic surface active agent, for example 0.1% of Triton X-100 (Rohm & Haas Co.). Consequently, the cell thus prepared may be used as such as an enzyme preparation.

The present invention will be illustrated in more detail with reference to the following experimental examples.

Experimental example 1

Production of NADH from NAD

Reaction for the production of NADH was carried out under the following standard condition: 3 mg of L-malic acid, 45 mg of $MgCl_2$ and 10 mg of NAD were dissolved in 2.0 ml of a 55 mM HEPES buffer solution; the solution obtained was adjusted to a pH of 7.4; and 1 ml of the enzyme solution was added, and reaction was carried out at 30° C. When 1.5 units of malate dehydrogenase of *Pseudomonas diminuta* IFO-13182 was used under this standard condition (activity was measured with NAD as a coenzyme), NADH was formed with a conversion ratio of about 100% in 3 hours.

Reaction was repeated with different buffer solutions. The results of the reaction are shown in Table 1.

TABLE 1

Effect of buffer solutions on reduction of NAD

| Buffer solution (50 mM; pH, 7.8) | Reaction time (hr) | | | | | |
|---|---|---|---|---|---|---|
| | 0 | 1 | 2 | 3 | 4 | 5 |
| HEPES buffer solution | 1.00(0)* | 52.25(63.78) | 71.40(87.62) | 79.50(97.70) | 82.60(101.56) | 83.25(102.36) |
| Potassium phosphate buffer solution | 1.00(0) | 38.25(46.36) | 57.05(69.76) | 64.75(79.34) | 73.90(90.73) | 81.60(100.31) |
| Sodium phosphate buffer solution | 1.00(0) | 34.25(41.38) | 52.40(63.97) | 66.05(80.96) | 70.20(86.12) | 82.75(101.74) |
| Tris-hydrochloride buffer solution | 1.00(0) | 36.30(43.93) | 60.35(73.86) | 74.55(91.54) | 82.15(101.00) | 82.30(101.18) |
| Water | 1.00(0) | 16.85(19.79) | 27.05(32.42) | 39.50(47.92) | 51.50(62.85) | 58.70(71.81) |

*Absorbance of the reaction solution at 340 nm.
A numeral in parentheses shows a conversion ratio (%) of NAD to NADH.

As is apparent from Table 1, a HEPES or potassium phosphate buffer solution is suitable for this reaction.

Next, a conversion ratio of NAD to NADH was examined with different concentrations of malic acid. The results are shown in Table 2.

TABLE 2

Effect of malic acid concentrations on reduction of NAD

| Concentration of malic acid (M) | Reaction time (hr) | | | | | |
|---|---|---|---|---|---|---|
| | 0 | 1 | 2 | 3 | 4 | 5 |
| 0 | 1.00(0)* | 1.00(0) | 1.00(0) | 1.00(0) | 1.00(0) | 1.00(0) |
| 0.005 | 1.00(0) | 25.00(31.87) | 25.45(32.47) | 22.80(28.95) | 19.25(25.56) | 18.15(22.77) |
| 0.01 | 1.00(0) | 40.45(52.39) | 48.55(64.47) | 47.80(62.15) | 45.00(58.43) | 44.45(57.70) |
| 0.05 | 1.00(0) | 56.00(73.04) | 71.15(93.16) | 71.65(93.82) | 71.85(94.08) | 73.15(95.81) |
| 0.10 | 1.00(0) | 58.60(76.49) | 73.25(95.94) | 71.90(94.15) | 72.80(95.35) | 74.35(97.40) |
| 0.15 | 1.00(0) | 53.85(70.18) | 71.00(92.96) | 72.15(94.48) | 70.85(92.76) | 71.90(94.15) |
| 0.20 | 1.00(0) | 50.50(65.73) | 70.50(92.29) | 71.90(94.15) | 74.50(97.60) | 74.40(97.47) |
| 0.40 | 1.00(0) | 38.75(50.13) | 58.00(75.69) | 70.60(92.42) | 74.60(97.74) | 75.90(99.46) |
| 0.60 | 1.00(0) | 31.10(39.97) | 51.80(67.46) | 64.30(84.06) | 70.95(92.89) | 74.55(97.67) |
| 0.80 | 1.00(0) | 25.45(32.47) | 44.35(57.57) | 55.20(71.97) | 60.95(79.61) | 71.45(93.55) |

TABLE 2-continued

| Concentration of malic acid (M) | Effect of malic acid concentrations on reduction of NAD | | | | | |
|---|---|---|---|---|---|---|
| | Reaction time (hr) | | | | | |
| | 0 | 1 | 2 | 3 | 4 | 5 |
| 1.00 | 1.00(0) | 17.25(21.84) | 31.15(40.04) | 36.50(47.14) | 50.80(66.13) | 55.15(71.91) |

*Absorbance of the reaction solution at 340 nm.
A numeral in parentheses shows a conversion ratio (%) of NAD to NADH.

As is apparent from Table 2, concentrations of 0.05 to 0.2M are suitable for reduction under the reaction condition described above.

Next, a conversion ratio of NAD to NADH was examined with different concentrations of NAD. The results are shown in Table 3.

TABLE 3

| Concentration of NAD (%) | Effect of NAD concentrations on reduction of NAD | | | | | |
|---|---|---|---|---|---|---|
| | Reaction time (hr) | | | | | |
| | 0 | 1 | 2 | 3 | 4 | 5 |
| 0.05 | 0.10(0)* | 4.17(101.31) | 4.11(99.81) | 4.08(99.07) | 4.30(104.54) | 3.98(96.57) |
| 0.10 | 0.10(0) | 7.44(90.85) | 7.57(92.97) | 7.67(94.21) | 8.15(100.19) | 7.95(97.70) |
| 0.50 | 0.50(0) | 28.80(70.44) | 37.05(91.97) | 39.10(97.19) | 40.05(99.44) | 40.65(99.94) |
| 0.75 | 1.00(0) | 31.20(50.11) | 50.00(81.31) | 55.35(90.19) | 59.35(96.83) | 59.35(96.83) |
| 1.00 | 1.00(0) | 49.70(60.61) | 76.00(93.34) | 83.40(102.55) | 83.60(102.80) | 83.60(102.80) |
| 2.50 | 1.00(0) | 13.30(6.12) | 19.55(9.23) | 24.95(11.92) | 25.15(12.02) | 26.10(12.50) |
| 5.00 | 1.00(0) | 5.80(1.19) | 6.10(1.27) | 6.50(1.37) | 7.00(1.49) | 7.30(1.57) |

*Absorbance of the reaction solution at 340 nm.
A numeral in parentheses shows a conversion ratio (%) of NAD to NADH.

As is shown in Table 3, an optimum concentration of NAD under the reaction condition described above is 1.0%, a conversion ratio of 100% being obtained by 3 hours' reaction.

It can be seen from these results that optimum concentrations of malic acid and NAD are 0.3% and 1.0%, respectively, and that a pH range of 7.5 to 8.0 is suitable for this enzyme reaction.

50% Ethanol was added to the reaction solution to precipitate contaminants such as protein, and after removing the contaminants, 90% ethanol was added to the solution to precipitate NADH. The NADH was purified by washing it several times with ethanol of the same concentration. The purified preparation was confirmed to be NADH from coenzyme activity with glutathione reductase (EC 1.6.4.2), and its purity obtained from said activity was 95%.

Experimental example 2

Production of NADPH from NADP

Reaction for the production of NADPH was carried out under the following standard condition: 10 mg of L-malic acid, 45 mg of MgCl$_2$ and 10 mg of NADP were dissolved in 2.0 ml of a 55 mM HEPES buffer solution; the solution ontained was adjusted to a pH of 7.4; and 1 ml of the enzyme solution was added, and reaction was carried out at 30° C. When 1.5 units of malate dehydrogenase of *Pseudomonas diminuta* IFO-13182 was used under this standard condition (activity was measured with NADP as a coenzyme), NADPH was formed with a conversion ratio of about 100% in 3 hours.

Reaction was repeated with different buffer solutions. The results of the reaction are shown in Table 4.

TABLE 4

| Buffer solution (50 mM; pH, 7.8) | Effect of buffer solutions on reduction of NADP | | | | | |
|---|---|---|---|---|---|---|
| | Reaction time (hr) | | | | | |
| | 0 | 1 | 2 | 3 | 4 | 5 |
| HEPES buffer solution | 1.0(0)* | 33.90(48.25) | 57.55(82.94) | 68.20(98.56) | 67.95(98.20) | 69.20(100.03) |
| Potassium phosphate buffer solution | 1.0(0) | 40.40(57.79) | 54.25(78.10) | 64.75(93.50) | 71.80(103.40) | 71.20(102.96) |
| Sodium phosphate buffer solution | 1.0(0) | 22.15(31.02) | 40.85(58.45) | 53.05(76.34) | 71.35(103.18) | 71.10(102.82) |
| Tris-hydrochloride buffer solution | 1.0(0) | 27.05(38.21) | 44.75(64.17) | 57.35(82.65) | 70.50(101.94) | 71.05(102.74) |
| Water | 1.0(0) | 15.65(21.49) | 29.55(41.87) | 38.95(55.66) | 48.15(69.16) | 56.80(81.84) |

*Absorbance of the reaction solution at 340 nm.
A numeral in parentheses shows a conversion ratio (%) of NADP to NADPH.

As is apparent from Table 4, a HEPES or potassium phosphate buffer solution is suitable for this reaction.

Next, a conversion ratio of NADP to NADPH was examined with different concentrations of malic acid. The results are shown in Table 5.

TABLE 5

| Concentration of malic acid (M) | Effect of malic acid concentrations on reduction of NADP | | | | | |
|---|---|---|---|---|---|---|
| | Reaction time (hr) | | | | | |
| | 0 | 1 | 2 | 3 | 4 | 5 |
| 0 | 1.10(0)* | 1.10(0) | 1.10(0) | 1.00(0) | 1.10(0) | 1.00(0) |

TABLE 5-continued
Effect of malic acid concentrations on reduction of NADP

| Concentration of malic acid (M) | Reaction time (hr) | | | | | |
|---|---|---|---|---|---|---|
| | 0 | 1 | 2 | 3 | 4 | 5 |
| 0.005 | 1.00(0) | 21.70(32.39) | 24.70(37.09) | 24.70(37.09) | 23.30(34.90) | 23.15(34.66) |
| 0.01 | 1.00(0) | 32.45(49.22) | 40.70(62.13) | 41.00(62.60) | 43.30(66.20) | 43.40(66.35) |
| 0.05 | 1.00(0) | 39.05(59.55) | 55.25(84.90) | 58.90(90.61) | 58.55(90.06) | 59.75(91.94) |
| 0.10 | 1.00(0) | 39.80(60.72) | 55.20(84.82) | 57.15(87.87) | 59.70(93.43) | 60.15(92.57) |
| 0.15 | 1.00(0) | 38.85(59.23) | 57.20(87.95) | 64.00(98.59) | 64.50(99.38) | 65.00(100.16) |
| 0.20 | 1.00(0) | 31.05(47.03) | 50.10(76.84) | 56.10(86.23) | 66.25(102.11) | 65.30(100.63) |
| 0.40 | 1.00(0) | 24.80(37.25) | 40.35(61.58) | 48.20(73.87) | 52.05(79.89) | 59.85(92.10) |
| 0.60 | 1.00(0) | 19.25(28.56) | 31.95(48.44) | 39.35(60.02) | 42.95(65.65) | 49.10(75.28) |
| 0.80 | 1.00(0) | 14.10(20.50) | 23.55(35.29) | 32.15(48.75) | 35.95(54.70) | 40.65(62.05) |
| 1.00 | 1.00(0) | 11.00(15.65) | 16.85(24.80) | 23.35(34.98) | 25.40(38.19) | 28.75(43.43) |

*Absorbance of the reaction solution at 340 nm.
A numeral in parentheses shows a conversion ratio (%) of NADP to NADPH.

As is apparent from Table 5, concentrations of 0.05 to 0.2M are suitable for reduction under the reaction condition described above.

Next, a conversion ratio of NADP to NADPH was examined with different concentrations of NADP. The results are shown in Table 6.

TABLE 6
Effect of NADP concentrations on reduction of NADP

| Concentration of NADP (%) | Reaction time (hr) | | | | | |
|---|---|---|---|---|---|---|
| | 0 | 1 | 2 | 3 | 4 | 5 |
| 0.05 | 0.10(0)* | 3.19(90.64) | 3.20(90.94) | 3.30(93.87) | 3.45(98.27) | 3.25(92.40) |
| 0.10 | 0.10(0) | 6.29(90.79) | 6.47(93.43) | 6.66(96.22) | 6.85(99.00) | 6.66(96.23) |
| 0.50 | 0.50(0) | 16.30(46.35) | 25.15(72.31) | 28.90(83.31) | 30.15(86.98) | 33.33(96.30) |
| 0.75 | 1.00(0) | 21.65(40.38) | 35.65(67.76) | 43.35(82.82) | 47.15(90.25) | 48.00(91.91) |
| 1.00 | 1.00(0) | 30.40(43.12) | 45.15(64.76) | 50.45(72.53) | 66.50(96.07) | 68.00(98.27) |
| 2.50 | 1.00(0) | 8.10(4.17) | 10.40(5.51) | 9.70(5.10) | 11.65(6.25) | 11.65(6.25) |
| 5.00 | 1.00(0) | 5.45(1.31) | 5.75(1.39) | 5.60(1.35) | 5.60(1.35) | 6.35(1.57) |

*Absorbance of the reaction solution at 340 nm.
A numeral in parentheses shows a conversion ratio (%) of NADP to NADPH.

As is shown in Table 6, an optimum concentration of NADP under the reaction condition described above is 1.0%, a conversion ratio of 100% being obtained by 4 hours' reaction.

It can be seen from these results that optimum concentrations of malic acid and NADP are 0.3% ad 1.0%, respectively, and that a pH range of 7.5 to 8.0 is suitable for this enzyme reaction.

50% Ethanol was added to the reaction solution to precipitate contaminants such as protein, and after removing the contaminants, 90% ethanol was added to the solution to precipitate NADPH. The NADPH was purified by washing it several times with ethanol of the same concentration. The purified preparation was confirmed to be NADPH from coenzyme activity with glutathione reductase (EC 1.6.4.2), and its purity obtained from said activity was 95%.

The present invention will be illustrated more specifically with reference to the following examples, but it is not limited to these examples.

EXAMPLE 1

A medium comprising 1 g/dl of DL-malic acid, 0.03 g/dl of $MgSO_4 \cdot 7H_2O$, 0.3 g/dl of citric acid, 1.5 g/dl of $K_2HPO_4$, 0.53 g/dl of $Na(NH_4)HPO_4$, 0.6 g/dl of NaOH, 0.1 g/dl of yeast extract and 1 g/dl of peptone was added to two 2-liter flasks at a rate of 500 ml per flask and sterilized at 120° C. for 15 minutes. Each medium was inoculated with *Pseudomonas diminuta* IFO-13182, followed by shaking culture at 30° C. for 24 hours. After the culture was finished, the culture broth was centrifuged to collect the cell. The cell was washed, suspended in 200 ml of a 40 mM phosphate buffer solution (pH, 7.4) containing 10 mM of 2-ME and 2 mM of EDTA-2Na and disintegrated at 5° C. for 10 minutes by means of a 9 KHz ultrasonic disintegrator. The solution after disintegration was centrifuged to obtain a supernatant solution. The solution was then heat-treated at 50° C. for 1 hour to deactivate NADH oxidase and used as an enzyme solution (EC 1.1.1.39).

6 Grams of L-malic acid, 3 g of $MgCl_2$ and 20 g of NAD were dissolved in 1.8 liters of a 55 mM potassium phosphate buffer solution, and the pH of the resulting solution was adjusted to 7.5. Thereafter, 200 ml of the enzyme solution was added, and reaction was carried out at 30° C.

NAD was reduced into NADH almost completely by continuing the reaction for 6 hours. After 6 hours, the reaction solution was lyophilized to obtain a powder which was then re-dissolved in 200 ml of distilled water. After removing insoluble products by centrifugation, the same amount of ethanol was added (50%), and formed precipitates were removed by centrifugation.

Ethanol was added to the supernatant solution obtained by centrifugation so that its concentration was 90%, to precipitate NADH. The precipitated NADH was washed three times with 90% ethanol.

The purity of the purified NADH thus obtained was about 95% from coenzyme activity with lactate dehydrogenase and absorption spectrum. Yield, 98%.

EXAMPLE 2

A solution subjected to ultrasonic disintegration was obtained in the same manner as in Example 1 and used as an enzyme solution.

6 Grams of L-malic acid, 3 g of $MgCl_2$ and 20 g of NADP were dissolved in 1.8 liters of a 55 mM potassium phosphate buffer solution, and the pH of the resulting solution was adjusted to 7.5. Thereafter, 200 ml of the enzyme solution was added, and reaction was carried out at 30° C.

NADP was reduced into NADPH almost completely by continuing the reaction for 5 hours.

After 5 hours, the reaction solution was lyophilized to obtain a powder which was then re-dissolved in 200 ml of distilled water. After removing insoluble products by centrifugation, the same amount of ethanol was added (50%), and formed precipitates were removed by centrifugation.

Ethanol was added to the supernatant solution obtained by centrifugation so that its concentration was 90%, to precipitate NADPH. The precipitated NADPH was washed three times with 90% ethanol. The purity of the purified NADPH thus obtained was about 96% from coenzyme activity with glutathione reductase and absorption spectrum. Yield, 99%.

EXAMPLE 3

To a reaction vessel was added 500 ml of a 50 mM phosphate buffer (pH, 7.5) containing 10 mM of $MgCl_2$, and after adding 5 g of NAD and 1.5 g of L-malic acid thereto, the pH of the resulting solution was adjusted to 7.5 with 1N NaOH. Thereafter, 50 units of malate dehydrogenase (EC 1.1.1.38) prepared from *Escherichia coli* by the method described in The Journal of the Biochemistry, Vol. 73, 169–180 (1973) was added, and reaction was carried out at 30° C. for 5 hours with gentle stirring. The pH at the end of the reaction was 7.8.

NAD and NADH in the reaction solution were determined by high-performance liquid chromatography to find that 95%, on calculation, of NAD initially present was reduced. To the reaction solution obtained was added 1000 ml of ethyl alcohol, and after standing still for 30 minutes, the enzyme was removed by centrifugation on a cooling centrifuge. Thereafter, ethyl alcohol was added to the supernatant solution until its concentration was 90%, and the solution was allowed to stand for 2 hours. The formed NADH precipitate was collected by centrifugation, washed with two portions of ethyl alcohol and two portions of ethyl ether, and vacuum-dried to obtain 4.5 g of NADH. The purity of the NADH was 97% by analysis with lactate dehydrogenase.

EXAMPLE 4

To a reaction vessel was added 500 ml of a 50 mM phosphate buffer (pH, 7.5) containing 10 mM of $MgCl_2$, and after adding 5 g of NAD and 1.5 g of L-malic acid thereto, the pH of the resulting solution was adjusted to 7.5 with 1N NaOH. Further, 50 units of malate dehydrogenase of *Escherichia coli* origin obtained in the same manner as in Example 3 was added, and reaction was carried out at 30° C. for 5 hours under reduced pressure (20 mmHg) with gentle stirring. The pH at the end of reaction was 8.0.

NAD and NADH in the reaction solution were determined by high-performance liquid chromatography to find that 98%, on calculation, of NAD initially present was reduced. To the reaction solution obtained was added 1000 ml of ethyl alcohol, and the enzyme was removed by centrifugation on a cooling centrifuge. Thereafter, ethyl alcohol was added to the supernatant solution until its concentration was 90%, and the solution was allowed to stand for 2 hours. The formed NADH precipitate was collected by centrifugation, washed with two portions of ethyl alcohol and two portions of ethyl ether, and vacuum-dried to obtain 4.8 g of NADH. The purity of the NADH was 98% by analysis with lactate dehydrogenase.

EXAMPLE 5

To a reaction vessel was added 1000 ml of water containing 10 mM of $MgCl_2$, and after adding 10 g of NADP and 3 g of L-malic acid, the pH of the resulting solution was adjusted to 7.5 with 1N NaOH. Further, 100 units of malate dehydrogenase (EC 1.1.1.40) prepared from pegion liver by the method described in Method in Enzymology, Vol. 1, 739–753, published from Academic Press Co. in 1955 was added, and reaction was carried out at 30° C. for 4 hours with gentle stirring. The pH at the end of reaction was 8.0.

NADP and NADPH in the reaction solution were determined by high-performance liquid chromatography to find that 98%, on calculation, of NADP initially present was reduced. To the reaction solution obtained was added 2000 ml of ethyl alcohol, and the enzyme was removed by centrifugation (15000×g, 20 minutes) on a cooling centrifuge. Thereafter, ethyl alcohol was added to the supernatant solution until its concentration was 90%, and the solution was allowed to stand for 2 hours. The formed NADPH precipitate was collected by centrifugation, washed with two portions of ethyl alcohol and two portions of ethyl ether, and vacuum-dried to obtain 9.3 g of NADPH. The purity of the NADPH was 96% by analysis with glutathione reductase.

What is claimed is:

1. A method for producing a reduced-form coenzyme which comprises reacting malic acid selected from the group consisting of L-malic acid and D,L-malic acid with one member selected from the coenzyme group consisting of nicotinamide adenine dinucleotide and nicotinamide adenine dinucleotide phosphate in the presence of malate dehydrogenase to obtain the corresponding reduced product.

2. A method as described in claim 1, wherein the reaction is carried out under reduced pressure while removing carbon dioxide gas, formed during the reaction, from the reaction system.

3. A method as described in claim 1 in which the malate dehydrogenase is Enzyme No. EC 1.1.1.38.

4. A method as described in claim 1 in which the malate dehydrogenase is Enzyme No. 1.1.1.39.

5. A method as described in claim 1 in which the malate dehydrogenase is Enzyme No. 1.1.1.40.

* * * * *